US005472699A

United States Patent [19]
Duffy et al.

[11] Patent Number: 5,472,699
[45] Date of Patent: Dec. 5, 1995

[54] COMPOSITION AND METHOD FOR VISIBLY REDUCING THE SIZE OF SKIN PORES

[75] Inventors: John A. Duffy, West Milford, N.J.; Alexander P. Znaiden, Sloatsburg, N.Y.

[73] Assignee: Avon Products, Inc., Suffern, N.Y.

[21] Appl. No.: 380,347

[22] Filed: Jan. 27, 1995

Related U.S. Application Data

[63] Continuation of Ser. No. 238,978, May 6, 1994, Pat. No. 5,415,861, which is a continuation of Ser. No. 986,814, Dec. 8, 1992, abandoned, which is a continuation of Ser. No. 724,104, Jul. 1, 1991, abandoned.

[51] Int. Cl.$^6$ ................................................ A61K 7/035
[52] U.S. Cl. .................... 424/401; 424/45; 424/78.02; 424/78.03; 424/724; 424/696; 424/195.1; 424/59; 514/944; 514/945; 514/937
[58] Field of Search ...................... 424/195.1, 401, 424/78.02, 78.03, 59, 724, 45, 6.96; 514/944, 945, 937

[56] References Cited

U.S. PATENT DOCUMENTS

| | | | |
|---|---|---|---|
| 4,643,939 | 2/1987 | Sugiyama et al. | 424/401 |
| 4,913,896 | 4/1990 | Harvey | 424/401 |
| 4,921,701 | 5/1990 | Blank | 424/401 |
| 4,933,177 | 6/1990 | Grollier et al. | 424/401 |
| 4,954,532 | 9/1990 | Elliott et al. | 424/70.1 |

FOREIGN PATENT DOCUMENTS 4-305512  10/1992  Japan .

OTHER PUBLICATIONS

Chemical Abstracts, vol. 80, No. 17, Item. No. 93053j. (1974).

Chemical Abstracts, vol. 108, No. 14, Item 118754a. (1988).

*Primary Examiner*—Raj Bawa
*Attorney, Agent, or Firm*—Hopgood, Calimafde, Kalil & Judlowe

[57] ABSTRACT

A method for reducing the visible size of facial skin pores by applying a novel composition which comprises an oil absorbing powder, a botanical astringent and a biological compound that alters the structure of the skin and/or the function of the sebaceous glands.

7 Claims, No Drawings

COMPOSITION AND METHOD FOR VISIBLY REDUCING THE SIZE OF SKIN PORES

RELATED APPLICATIONS

This is a continuation of application Ser. No. 08/238,978 filed May 6, 1994, now U.S. Pat. No. 5,415,861 issued on May 16, 1995, which is a continuation of application Ser. No. 07/986,814 filed Dec. 8, 1992, now abandoned, which is a continuation of application Ser. No. 07/724,104 filed Jul. 1, 1991, now abandoned.

FIELD OF THE INVENTION

This invention relates to novel topical compositions for visibly reducing the size of enlarged skin pores, and to a method for using these compositions to improve the overall appearance of skin.

BACKGROUND OF THE INVENTION

Human skin is a permeable membrane. It is characterized by thousands of pores which function as openings for sebaceous (oil producing) and eccrine (sweat-producing) glands located beneath the skin. Each pore communicates with a corresponding gland by means of a hollow tube, otherwise known as the pilary canal. According to this configuration, a pore functions as an exit portal for internally produced sebaceous and sweat gland products such as sebum (oil) and perspiration. Skin pores also represent entry portals for externally applied substances, including lotions, creams and cosmetic preparations. It is generally understood that human skin represents a changing, dynamic environment where the exit and entry of substances can significantly influence pore size and visibility.

Pores associated with sweat glands are very small. There are no aesthetic considerations because these skin surface openings are not visible without a magnifying lens. The present invention is directed to the size and visibility of skin pores that communicate with more troublesome sebaceous glands. These pores provide the situs for surface ache which creates a coarse and uneven appearance on the skin.

Skin pores (and sebaceous glands) are large and numerous on the face and scalp, coincidentally the areas of maximum exposure on the skin. For facial areas the density ranges from 400 to 800 pores/$cm^2$, compared with 50 pores/$cm^2$ on the arms and legs. The forehead, nose and nasolabial folds are the areas of highest pore concentration.

Pores, like wrinkles, have a defined size which is susceptible to measurement. But; the visual appearance of skin pores partially depends on the texture of surrounding surfaces. A rough, dry condition scatters light in a manner which emphasizes openings on the skin surface. In contrast, smooth skin reflects incident light to reduce the appearance of surface irregularities created by pores or openings. When a pore is surrounded by rough, debris-laden skin it is more noticeable and appears larger.

In scientific terms, the skin pore of interest is known as a "follicular orifice." The orifice or pore cooperates with a sebaceous follicle characterized by a small, hair-producing portion, a deep pilary canal and a multilobular sebaceous gland that secretes its product (sebum or "oil") into the base of the canal.

The upper most portion of the pilary canal is lined with a layer of "horny cells" which are constantly replaced and shed into the canal. Under normal circumstances, the displaced cells mix with sebum that flows through the canal and onto the skin surface. This dynamic process of descaling and cleansing with sebum occurs on a continuous basis.

Pore size is largely determined by genetic, environmental and physiological factors. It is generally understood that pore diameter is proportionate to the size of sebaceous glands beneath the skin. A good correlation is recognized between pore size and oil-producing activity. Large pores (orifices) create a coarse, uneven complexion which generally detracts from the appearance of an individual.

Increased pore size is frequently associated with hyperactive sebaceous glands. This condition generates larger amounts of sebum which expands the pilary canal and dilates pore diameter to accommodate greater internal pressure. By limiting sebum production and/or facilitating sebum removal, the compositions of the present invention minimize pore size and improve overall appearance.

It will also be appreciated that the sebaceous follicle may produce cells which do not shed as fine, discrete particles. When this condition occurs, the cells accumulate, coagulate with sebum, mix with other skin materials and "plug" the pore opening. This aberration disrupts the normal environment of cellular shedding and cleansing with sebum secretions. It also leads to an accumulation of cellular debris, enlargement of the attendant pore and greater visibility on the skin surface.

The aging process further increases pore size and visibility. During adolescence, larger pores are generally attributed to increased glandular activity and higher sebum production which causes canal blockage and pore expansion. As the aging process continues, sebum production gradually declines and the shedding of "horny cells" slows down. These conditions cause an accumulation of debris which increases the size and visibility of individual pores.

The aging process also causes deterioration of the dermal elements surrounding the follicle. These changes are manifested by internal collapse of supporting skin structure and expansion of the follicular canal. The ultimate result is pore dilation and greater visibility on the skin surface.

The skin pore reducer of this invention prevents accumulation of oil and other debris in the pilary canal, at the pore opening and on the surrounding skin surface. This cleansing technique "shrinks" the pore and minimizes visibility on the skin surface.

Numerous art-recognized compositions have attempted to absorb oil and facial debris from skin surfaces and attendant pore structures. Examples of these products are described in Groller U.S. Pat. No. 4,933,177 and Elliott U.S. Pat. No. 4,954,532. But, the prior art has not identified or addressed the multiple causes of skin pore enlargement.

OBJECTS OF THE INVENTION

Accordingly, it is an object of this invention to provide topically applied compositions that reduce the size of visible skin pores.

It is an additional object of the present invention to provide compositions which inhibit the rate of sebum production in the sebaceous follicles.

It is a further object of the present invention to provide compositions which facilitate removal of sebum, oil, dirt and skin debris from pore openings and surrounding surfaces.

Yet another object of the present invention is to provide compositions which enhance dermal matrix qualities directed to elasticity and structural firmness.

It is a further object of the present invention to provide an over-the-counter formulation which is readily available to the retail consumer.

Another object of the present invention is to provide a prepared composition which can be topically applied without the attention of a licensed physician.

SUMMARY OF THE INVENTION

The present invention provides a method and compositions for reducing the size of visible skin pores. Active ingredients absorb and remove "oil" (sebum). This cleansing operation temporarily reduces internal pressure which dilates or expands the follicular canal and attendant pore opening.

The described compositions also reduce the cohesion of "horny cells" which are continuously shed into the follicular canal and secreted onto the skin surface without "plugging" individual pores. Skin debris is loosened and removed from pores and surrounding areas to achieve smoother complexions with smaller, less visible pore structure. The method of treatment preferably involves topical application, intermediate drying and removal of effective compositions.

To accomplish these and other benefits, this invention provides compositions which comprise an oil absorbing powder, a botanical astringent and a biological. Described compositions cleanse skin pore openings, support the dermal matrix and regulate secretions from the sebaceous glands. By practicing the disclosed method, these compositions cause a visual reduction in the size of skin pores on the face and other areas of the body.

DETAILED DESCRIPTION OF SPECIFIC EMBODIMENTS

The novel compositions of this invention comprise three classes of essential ingredients, preferably in a suitable carrier. The three classes are generally defined as oil absorbing powders, botanical astringents and biologicals that influence the structure of the dermal matrix and/or the sebaceous glands.

The oil absorbing powder is any substance which is capable of removing oil secretions from a skin pore and its surrounding surface. Exemplary oil absorbing powders include those made from bentonite, rice starch, silica, calcium sulfate and mixtures thereof. The oil absorbing powder is present in an amount from 10 to 30 wt. %, preferably in an amount from 15 to 25 wt. %.

Bentonite is a native, colloidal, hydrated aluminum silicate, otherwise known as white clay. As provided commercially, bentonite particles typically range in size from 1 to 150 μm. Each particle can absorb approximately one-half its weight in excess oil. Bentonite is a preferred ingredient because it contributes skin softening properties to compositions of the present invention (Harry, *Cosmetic Materials*, Vol. 2, London, 1950). A particularly useful form is sold under the tradename Microfine Bentonite. It is further described in trade literature distributed by American Colloid Company, Arlington Heights, Ill.

Rice starch is another preferred oil absorbing powder. Previously, rice starch was used in cosmetics as a binding agent for face powders. It is provided by treating rice grains with caustic soda, which dissolves the gluten and precipitates the starch granules. Although rice starch has been known to absorb moisture, we have discovered an unexpected capacity to absorb its full weight in oil. When mixed with glycerin, rice starch has the added benefit of providing a soothing, protective composition which effectively absorbs oil without overstripping the skin. These properties are described by Greenberg & Lester, *Handbook of Cosmetic Materials*, Wiley-Interscience, New York, 1954.

Silica is also useful in compositions of the present invention. These materials are commercially available in several grades or particle sizes. Suitable products are sold by Cabot Corporation, Tuscola, Ill. under the trade designation Cab-O-Sil. Cab-O-Sil EH-5 is especially preferred with a nominal particle diameter of 0.007 μm and a specific surface area of approximately 380±30 $m^2/g$. The high surface area is expected to increase oil absorbency. Conventional testing indicates that EH- 5 can absorb more than four times its weight in skin surface oils.

Like the other oil-absorbing powders of the present invention, effective amounts of calcium sulfate remove skin surface oil and withdraw excess sebum from the pilary canal.

Compositions of this invention also include a biological astringent as the second major component. Botanicals have been used topically and systemically for over 5,000 years. Anticipated medicinal benefits were historically based on folklore. But, modern analytical techniques now identify constituent compounds and provide scientific explanations for related benefits to the dermal matrix.

According to the present invention, representative botanical astringents include extracts from herbs such as Horsetail, Witch Hazel, St. John's Wort, Balm Mint and Linden. Mixtures of these extracts are also contemplated. The botanical is present in an amount from 0.01 to 10 wt. %, preferably in an amount from 0.1 to 1.0 wt. %.

Witch Hazel (*Hamamelis virginiana*) extracts have art-recognized astringent and cleansing properties which are useful for cosmetic preparations. The astringent effect is provided by a relatively high (8–12%) concentration of tannins found in the leaves and bark. Witch Hazel extracts also contain saponins, a sugar-steroid alcohol complex which exhibits high surface activity. This property improves she cleansing function and facilitates removal of dirt, oil and debris from skin pores and surrounding surfaces.

Another astringent botanical extract is derived from Linden (*Tilia platyphyllos*). Linden extracts contain several constituents responsible for immediate and long-term benefits in the treatment of oily skin and large pores. Tannins, citral and a complex mixture of fatty oils provide immediate astringent and cleansing benefits.

Long-term benefits are derived from the Vitamin C, Vitamin E and farnesol content in Linden extracts. Farnesol is a precursor to squalene, a normal product of the sebaceous glands. An increased concentration of farnesol can be expected to moderate sebum sec-retions. Vitamin C is essential to the production of collagen, a critical component of the dermal matrix. Vitamin E is an anti-oxidant for the collagen matrix. This anti-oxidant function is enhanced by the synergistic effect of Vitamin C present in the extract. By protecting the quality of the dermal matrix, Linden extracts improve skin texture and reduce the size of visible skin pores. See, e.g., Kaplan, "A New Stabilized Ascorbic Acid Solution: Percutaneous Absorption and Effect on Relative Collagen Synthesis," *J. Cutaneous Aging & Cosmetic Dermatology*, Vol. 1, No. 2, pp. 115–121 (1988/1989); Tojo, "Skin Penetration of Vitamins C and E," *J. Soc. Cosmet. Chem.*, Vol. 40, pp. 119–125 (March/April 1989).

St. John's Wort (*Hypericum performatum*) is a suitable cosmetic astringent based on relatively high concentrations of tannins in the extract. The botanical also contains the Bioflavonoid rutin, a naturally occurring anti-oxidant. Significant amounts of Vitamin A are present to suppress sebum production and reduce the size of large skin pores. Vitamin C concentrations provide the same beneficial properties described in connection with Linden extracts.

Extract from Balm Mint (*Melissa officinalis*) offers similar astringent properties based on the presence of tannins and citral as principal constituents. This extract also contains Bioflavinoids which protect the dermal matrix and provide previously described advantages.

Horsetail extract (*Equisetum arvense*) is a preferred compound because it contains significant amounts (>8%) of organic silicones. These silicones are known to regulate collagen cross-linking and improve the structural framework of connective tissues in the skin. Like the alternative compositions, Horsetail extract functions on and below the skin surface to reduce pore size with regular application.

Active biologicals are the third essential component of the present invention. Specific materials are selected for their ability to normalize and regulate sebum production. These biologicals also free the pilary canal of pore-clogging dirt and skin debris. By way of illustration, representative biologicals include salicylic acid, farnesyl acetate, panthethine triacetate, pyridoxine hydrochloride, biotin, lysine carboxymethyl cisteinate and mixtures thereof. The biological compound is present in an amount from 0.01 to 10 wt. %, preferably in an amount of from 0.05 to 0.5 wt. %.

Pyridoxine HCl is an interchangeable form of Vitamin $B_6$, a preferred dietary supplement not synthesized by the human body. Although not well understood, it is anticipated that Vitamin $B_6$ deficiencies cause increased production of fatty acids in the sebaceous gland which enlarge the pilary canal and corresponding skin pore. Empirical observations indicate that skin supplementation of Vitamin $B_6$ (pyridoxine HCl) reduces sebum production and limits pore size.

Recent evidence also suggests that pyridoxine plays an important role in collagen and elastin cross-linking. Roe, *Nutrition and the Skin*, Alan R. Liss, Inc., 1986. Proper cross-linking of these proteins influences the quality of the dermal matrix as previously described. A pyridoxine deficiency reduces cross-linking and increases pore size by destabilizing the skin structure.

Another preferred biological is biotin, a water-soluble B vitamin. Biotin deficiencies reportedly cause seborrheic dermatitis. It is also reported that Biotin acts synergistically with Vitamin $B_6$ to maintain normal fatty acid synthesis and regulate sebum production. d-Biotin is otherwise expressed as Cis-hexahydro-2-oxo-1H-thieno-(3,4)-imidazole-4-valeric acid. Suitable compounds are available from Hoffmann-La Roche Inc., Roche Chemical Division, Nutley, N.J.

Salicylic acid is an alternative biological which accelerates the removal of horny cells by decreasing their "stickiness" or cohesion. See, Roberts, "Detection of the Action of Salicylic Acid on the Normal Stratum Corneum," *Brit. J. Derm.*, Vol. 103, page 191 (1980). It will be appreciated that skin pores are smaller in appearance following the removal of horny cells from the pore opening and surrounding skin surface.

Farnesyl acetate and panthenyl triacetate form a unique bioactive complex which regulates secretions from the sebaceous glands. Farnesol and farnesol derivatives are naturally occurring substances which act as precursors and intermediates in the biosynthesis of squalene and sterols, specifically cholesterol. Additional disclosure is provided by *Induchem Technical Bulletin*, "Unitrienol T-27," Induchem AG Dübendorf, Germany. Squalene and cholesterol are produced only by the sebaceous glands, and controlling their rate of production is critical to regulating overall sebum production.

Lysine carboxymethyl cisteinate is a carefully balanced complex which regulates sebum secretions as shown by clinical demonstrations. While the mechanism for this action is not completely understood, reduced pore size has been observed following use of treatment products containing this active ingredient.

According to the present invention, the oil absorbing powder, botanical extract and biological compound are admixed with a suitable vehicle or carrier system. Preferred carriers include water, ethyl alcohol, isopropyl alcohol, glycerin and mixtures thereof which are present in concentrations sufficient to dissolve and/or disperse the various components. A suitable delivery system will preferably dry in a reasonably short period of time (15–20 minutes maximum). It should be water-soluble and easily removed by rinsing.

It will be appreciated that a topical delivery system may include lotions, ointments, salves, creams, gels, foams, sprays and the like. Physical carriers may also take the form of patches or masks which are known in the art. Further additions are contemplated provided that they are compatible with the active ingredients and do not adversely affect the desired function. Additional components may include well-known colorants, fragrances, thickeners, Preservatives, humectants, surfactants, dispersants and the like, The invention will now be further described with reference to the following broad example which is provided for illustrative, not limiting purposes.

|  | % (w/w) |
| --- | --- |
| demineralized water | q.s. |
| glycerin | 5.0 |
| alcohol | 13.0 |
| thickener | 0.5 |
| surfactants | 3.0 |
| oil absorbing powder | 21.0 |
| botanical extract(s) | 0.5 |
| biological | 0.212 |
| colorant(s)/fragrance/preservative | q.s. |

The abbreviation "q.s." is standard dispensing nomenclature which means "as needed" or "as sufficient." During practical application, water, colorants, fragrances, preservatives and the like are added to the composition for cosmetic and/or aesthetic purposes. For example, viscosity can be varied with the amount of water. A viscous composition will dry faster based on reduced water content. Higher alcohol concentrations will also accelerate the drying or evaporation process.

The novel method of the present invention is practiced by applying a described composition to the face (or other skin surface), allowing the applied composition to dry completely and rinsing or otherwise removing the dried composition from the skin surface, preferably with water.

The composition is generally formulated to dry within 15–20 minutes. When applied as a mask, the preferred composition dries in approximately 15 minutes, as indicated by a distinct color change. After a single application pore size is visibly reduced and the skin displays a smoother, more refined texture. Regular applications will maintain these preferred characteristics.

This specification clearly illustrates the principles of the present invention. Based on this disclosure, numerous modifications will be readily apparent to those skilled in the art. These modifications are within the scope and spirit of the present invention as defined by the following claims.

What is claimed is:

1. A composition for visibly reducing the size of skin pores, consisting essentially of:

10 to 30 wt. % of an oil absorbing powder having an average particle size of less than 1.0 μm, said powder selected from the group consisting of silica, rice starch, bentonite, calcium sulfate and mixtures thereof;

0.01 to 10 wt. % of a botanical astringent selected from the group consisting of an extract from *Equisetum arvense*, Hamamelis, *vaginiana, Hypericum performatum, Melissa officinalis, Tilia platyphyllos* and mixtures thereof;

0.01 to 10 wt. % of a biological compound capable of regulating sebum production and clearing pilary canals, said compound selected from the group consisting of salicylic acid, farnesyl acetate, panthetine triacetate, pyridoxine hydrochloride, biotin, lysine carboxymethyl cisteinate and mixtures thereof; and a topically acceptable carrier.

2. The composition of claim 1, further consisting of at least one additive selected from the group consisting of colorants, fragrances, preservatives, thickeners, humectants and mixtures thereof.

3. The composition of claim 1, wherein said topically acceptable carrier is selected from the group consisting of water, ethyl alcohol, isopropyl alcohol, glycerin and mixtures thereof.

4. The composition of claim 1, further consisting a topical delivery system for said composition, said delivery system selected from the group consisting of lotions, ointments, creams, gels, foams, sprays, patches and masks.

5. The composition of claim 1, wherein said oil absorbing powder is 15 to 25 wt. % of said composition.

6. The composition of claim 1, wherein said botanical astringent is 0.05 to 1.0 wt. % of said composition.

7. The composition of claim 1, wherein said biological compound is 0.05 to 0.5 wt. % of said composition.

* * * * *